US00PP30964P3

(12) United States Plant Patent
Grisoni et al.

(10) Patent No.: US PP30,964 P3
(45) Date of Patent: Oct. 22, 2019

(54) *VANILLA* VARIETY NAMED 'HANDA'

(50) Latin Name: *Vanilla planifolia*
Varietal Denomination: Handa

(71) Applicant: French Agricultural Research Centre for International Development (CIRAD), Saint-Pierre (FR)

(72) Inventors: Michel Grisoni, Saint-Pierre (FR); Jean-Bernard Dijoux, Saint-Pierre (FR)

(73) Assignee: FRENCH AGRICULTURAL RESEARCH CENTRE FOR INTERNATIONAL DEVELOPMENT (CIRAD), Saint-Pierre (FR)

( * ) Notice: Subject to any disclaimer, the term of this patent is extended or adjusted under 35 U.S.C. 154(b) by 253 days.

(21) Appl. No.: 14/999,830

(22) Filed: Jul. 6, 2016

(65) Prior Publication Data

US 2017/0013762 P1 Jan. 12, 2017

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./263.1, 311
CPC ..... A01H 5/02; A01H 5/08; A01H 5/10
See application file for complete search history.

(56) References Cited

U.S. PATENT DOCUMENTS

PP28,912 P3 * 1/2018 Schoone ..... A01H 5/02 Plt./311

OTHER PUBLICATIONS

Bory et al., "Biodiversity and Preservation of *Vanilla*: Present State of Knowledge", Genetic Resources and Crop Evolution, vol. 55, 2008, pp. 551-571.
Bory et al., "Patterns of Introduction and Diversification of *Vanilla planifolia* (Orchidaceae) in Reunion Island (Indian Ocean)", American Journal of Botany, vol. 95, No. 7, Jul. 2008, pp. 805-815.
Castillo Martinez et al., "Caracterizacion De Dos Tipos De *Vanilla planifolia*", Acta Botánica Mexicana, vol. 25, 1993, pp. 49-59 (English Abstract Only).
Delassus, M., "La Lutte Contre La Fusariose Du Vanillier Par Les Méthodes Génétiques", 1963, pp. 245-246 (See Communication Under 37 CFR § 1.98(a) (3)).
Divakaran et al., "Interspecific Hybridization in *Vanilla* and Molecular Characterization of Hybrids and Selfed Progenies Using RAPD and AFLP Markers", Scientia Horticulturae, vol. 108, 2006, pp. 414-422.
Grisoni, Michel, "Phytosanitary Constraints on Bourbon *Vanilla*: Past and Present Situations and Perspectives for Control", *Vanilla*, Nov. 11-12, 2009, 46 pages.
Havkin-Frenkel et al., "Handbook of *Vanilla* Science and Technology", 2011, 26 pages.
Koyyappurath et al., "*Fusarium oxysporum* f. sp. Radicis-Vanillae is the Causal Agent of Root and Stem Rot of *Vanilla*", Plant Pathology, 2015, pp. 1-14.
Koyyappurath et al., "Differential Responses of *Vanilla* Accessions to Root Rot and Colonization by *Fusarium oxysporum* f. sp. Radicis-Vaniilae", Frontiers in Plant Science, vol. 6, No. 1125, Dec. 2015, pp. 1-16.
Murashige et al., "A Revised Medium for Rapid Growth and Bio Assays with Tobacco Tissue Cultures", Physiologia Plantarum, vol. 15, 1962, pp. 473-497.
Palama et al., "Metabolic Characterization of Green Pods from *Vanilla planifolia* Accessions Grown in La Réunion", Environmental and Experimental Botany, 2011, pp. 258-265.
Roux-Cuvelier et al., "Conservation and Movement of *Vanilla* Germplasm", *Vanilla*, 2010, pp. 31-41.
Silva et al., "New Insight on the Genesis and Fate of Odor-Active Compounds in *Vanilla* Beans (*Vanilla planifolia* G. Jackson) During Traditional Curing", Food Research International, vol. 44, 2011, pp. 2930-2937.
Soto Arenas et al., "Informe Final* Del Proyecto J101", 1999, 106 pages. (See Communication Under 37 CFR § 1.98(a) (3)).
Soto Arenas et al., "*Vanilla*", Vanilloideae, vol. 3, 2003, pp. 321-334.
Theis, T., "*Vanilla* Hybrid Resistant Fusarium Root Rot", Phytopathology, vol. 47, Oct. 1957, pp. 579-581.

* cited by examiner

*Primary Examiner* — Kent L Bell
(74) *Attorney, Agent, or Firm* — Birch, Stewart, Kolasch & Birch, LLP

(57) ABSTRACT

A new *vanilla* variety (*Vanilla planifolia, vanilla* orchid) designated as 'Handa' is provided that produces aromatic fruit having a suitable vanillin content and combines superior agronomic and technologic properties as compared to ordinary *vanilla*, notably resistance to *Fusarium oxysporum* f. sp. *radicis vanillae*, and indehiscence of the fruit.

3 Drawing Sheets

*VANILLA* VARIETY NAMED 'HANDA'

Latin name:

Botanical/commercial classification: (*Vanilla planifolia*), new *vanilla* cultivar.

Varietal denomination: The varietal denomination of the claimed *vanilla* variety is 'Handa'.

CROSS-REFERENCE TO RELATED APPLICATION

This application claims the benefit, under 35 U.S.C. 119, of Community Plant Variety Office (CPVO) Application No. 2015/1561, filed Jul. 7, 2015; which is incorporated herein by reference in its entirety.

BACKGROUND OF THE INVENTION

Commercial *vanilla* is produced by curing the mature fruits of *Vanilla planifolia* or *V.* x *tahitensis* (Orchidaceae). The largest portion of the *vanilla* marketed worldwide comes from *V. planifolia* and originates from the Indian Ocean region. Madagascar provides over 70% of the world's *vanilla* production, with the *vanilla* coming from small village plantations in the Northern provinces of this country. *Vanilla* is also produced in e.g. Indonesia (10%), Comoros (5%), India (5%), and Uganda (5%). The United States of America, Europe, and Japan are the main *vanilla* consumer countries. However, current world production of *vanilla*, which is about 2,500 tons/year, only partially meets the annual global demand for *vanilla*, which is estimated at more than 3,000 tons/year. This deficiency in *vanilla* supply is typically met by production of vanillin through synthesis or biosynthesis from various raw materials in order to accommodate demand.

*Vanilla planifolia* originated in Mexico and Central America. Some genetic diversity still exists in protected natural areas and farmer plots, but this diversity tends to diminish year after year (Soto Arenas 1999; Soto Arenas 2003). From its native region, very few *vanilla* varieties are cultivated and none of which have been accurately characterized (Roux-Cuvelier & Grisoni 2010). Global *vanilla* production is therefore based on an extremely narrow genetic base, which limits the possibilities of adapting to global changes (e.g. global climate change).

The premature fruit drop that dramatically impacts Mexican farmers in the Veracruz region is considered a harbinger of the impact of climate change on this traditional crop (Hernandez Hernandez 2011). In the Indian Ocean area, the increasing pressure of pests and diseases in production plots strongly hampers the *vanilla* industry (Grisoni et al. 2009). In particular, the root rot disease, caused by the soil borne fungus *Fusarium oxysporum* f. sp. *radicis vanillae* (Koyyappurath et al. 2015), has had severe impacts on the *vanilla* market since the 2000s.

Obtaining new genetic resources for *vanilla*, which are e.g. better adapted to the biotic and abiotic constraints while still meeting commercial requirements, is therefore an issue of primary importance for the global *vanilla* market and *vanilla* breeders. Indeed, *vanilla* remains one of the most requested and popular spices in the world. Accordingly, there exists a need for improved *vanilla* varieties with improved disease resistance and commercial viability as compared to other traditional *vanilla* varieties.

BRIEF SUMMARY

The present invention relates to a new and distinct *vanilla* cultivar (*Vanilla planifolia*) that has been denominated as 'Handa', and more particularly as a *vanilla* variety that produces aromatic fruit having a suitable vanillin content and combines superior agronomic and technologic properties as compared to ordinary *vanilla*, notably resistance to *Fusarium oxysporum* f. sp. *radicis vanillae*, and indehiscence of the fruit.

Applicant developed a breeding program for *vanilla* aimed at producing *vanilla* plants with disease resistance and having favorable agronomic properties. The high heterozygosity of *vanilla* plants inherited from their natural sexual reproduction that favors outcrossing (Soto Arenas 1999) suggested that new *vanilla* varieties could be recovered by recombination of characters in self-pollinated progenies. Applicant's *vanilla* breeding program involved self-pollination of the ordinary *vanilla* variety and selection of progeny with desirable characteristics. The present *vanilla* variety 'Handa' as described herein is a product of these breeding efforts, as outlined below.

In November of Year 1, an ordinary *vanilla* plant (*Vanilla planifolia*) being cultivated at La Bretagne (La Réunion, France) was manually auto-pollinated. Progeny seeds resulting from this self-pollination were collected from a mature fruit in June of Year 2, and these seeds were plated on Murashige and Skoog (MS) culture media (Murashige & Skoog 1962). Between February and May of Year 3, the germinated seeds (protocorms) were individually subcultured onto new MS media in tubes. Regular subculture of the 11 *vanilla* seedling lines recovered from the initial plates (accession numbers CR0019 to CR0029) took place from Year 4-Year 9. In Year 9, these 11 *vanilla* seedlings were transferred to a plant protection platform in Saint Pierre for conservation and acclimatization of the material. In Year 12, the acclimatized lines were planted into a shadehouse in La Réunion, France for field evaluation. The *vanilla* seedling designated CR0020 was selected and is presented herein as variety 'Handa'.

From Year 4 to Year 9, *vanilla* variety 'Handa' was maintained in vitro, and was asexually reproduced by micro-cuttings every 10th month, on MS medium, in the laboratory in La Bretagne (La Réunion, France). From Year 9 to the present, *vanilla* variety 'Handa' has been reproduced by micro-cuttings in vitro, on MS medium, at the laboratory of Saint Pierre, (La Réunion, France). After acclimatization of *vanilla* variety 'Handa' in Year 12, this variety was also asexually reproduced by cuttings and cultivated in a shadehouse in Saint Pierre. Between Year 18 and Year 20, *vanilla* variety 'Handa' was planted in three experimental plots of La Réunion for a multilocal trial in the municipalities of Sainte Rose, Saint Philippe, and Saint Andre.

BOTANICAL DESCRIPTION OF THE PLANT

Figure 1:
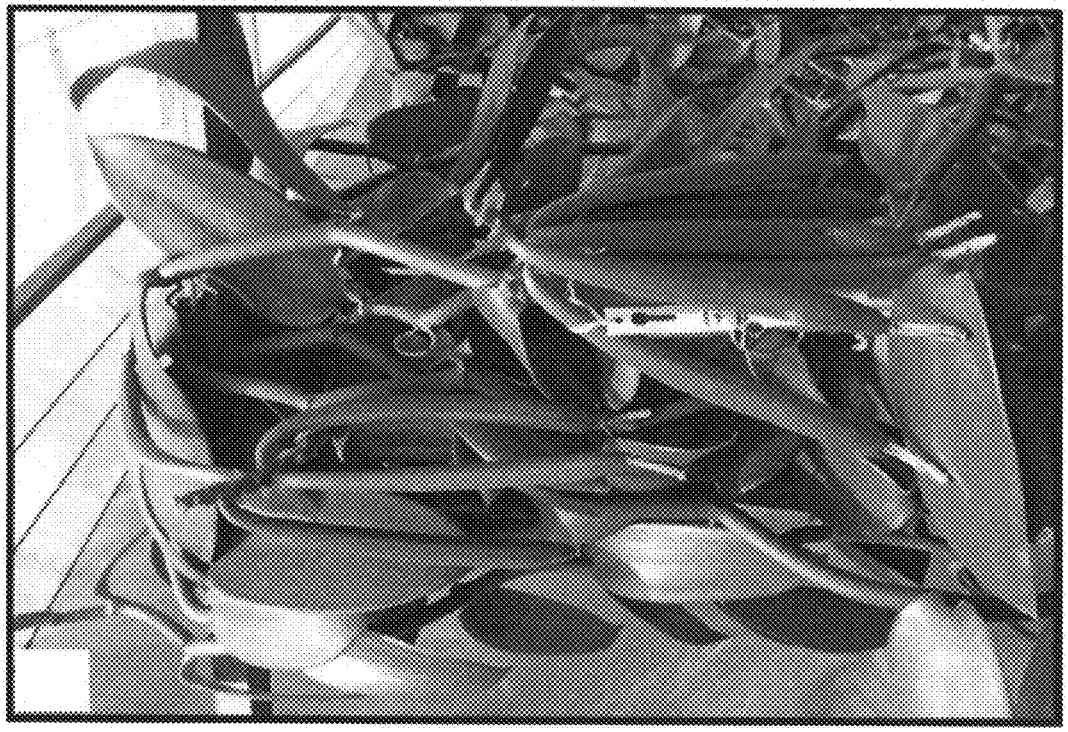
FIG. 1 illustrates vines of *vanilla* variety 'Handa' bearing young fruit.

The following is a detailed botanical description of the new *vanilla* variety designated as 'Handa', including the key differentiating characteristics of this variety and comparisons of certain characteristics of 'Handa' to other *vanilla* varieties.

*Vanilla planifolia* Jacks (ex Andrews), commonly called *vanilla*, is a hemi-epiphytic orchid vine that is native to Mexico and Central America. In its native habitat (rain forest), it may grow up to 10-30 m tall over time. The vine has a thick, fleshy stem (5 to 15 mm diameter) bearing alternate, succulent, flat-bladed elliptic leaves (20×15 cm L×1, 1-2 mm thick) and adventitious, aerial roots, which allow it to cling to its support. The leaves and stem are pale to dark green depending on light intensity. The vine generally produces greenish flowers once per year (about 5 cm wide) that open early in the morning and close in the afternoon. Due to a membrane called the rostellum that forms a physical barrier between the male and female organs in the flower, fertilization of the ovules by pollen should be assisted by a pollinator. In nature, pollination is accomplished by bees. In culture, *vanilla* flowers need to be hand pollinated in order to produce fruits. The fruits (15-23 cm long, 0.8-1.6 cm wide) reach maturity 8-10 months after pollination. A post-harvest curing of the fruits during 4 to 9 months is necessary to obtain the stable, aromatic and dry *vanilla* pods that constitute the commercial *vanilla*.

Since *vanilla* vines may be reproduced by cuttings (80-120 cm long stem fragment), they have been clonally propagated throughout the world by this method, and from few initial materials collected in Mexico (Bory et al. 2008b). As a consequence, the vast majority of the cultivated *vanilla* belong to the ordinary type, also called 'Classique' in Réunion Island, 'Mansa' in Mexico, and 'Gasy' in Madagascar. However, a few natural variants of *Vanilla planifolia* detected in farmers' plots have been described (Castillo Martinez & Engleman 1993; Bory et al. 2008a). Table 1 summarizes the main distinctive traits of these varieties.

TABLE 1

Comparison of vanilla varieties to ordinary vanilla

| Variety | Distinctiveness as compared to ordinary vanilla |
|---|---|
| 'Aifluille' | Lanceolate leaves, thin fruit and low vigor. |
| 'Mexique' | Slightly bigger fruits with rounded section, darker leaf color. |
| 'Varieflata' or 'Rayada' | Presence of white/yellow stripes on leaf, stem, fruit. |
| 'Grosse vanille' | Bigger and thicker leaves, bigger stem and flower (tetraploid), indehiscent fruit. |
| 'Male sterile' | Abortion of auto-pollinated fruits (triploid). |
| 'Oreja de burro' | Leaf, stem and flower are bigger, early blooming, abortion of auto-pollinated fruits. |

Interspecific hybrids have also been produced in Puerto Rico, Madagascar, and India (Theis & Jimenez 1957; Delassus 1963; Minoo et al. 2006). These plants have genetic, morphologic, and aromatic properties very distinct from those of *V. planifolia*.

Figure 2:
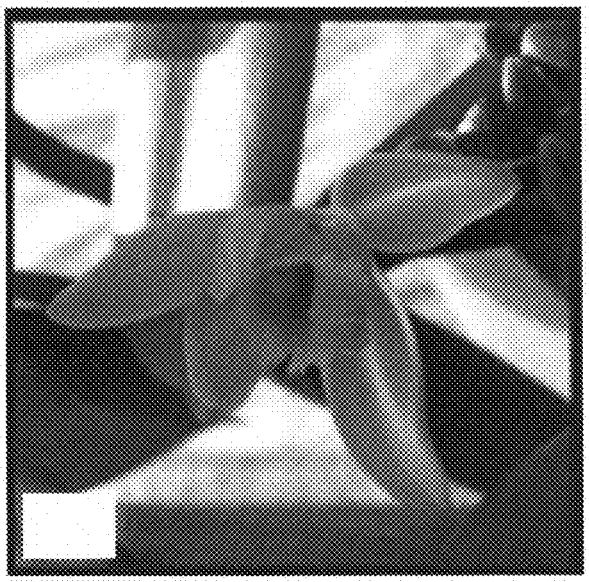
FIG. 2 illustrates a flower of *vanilla* variety 'Handa'.
Figure 3:
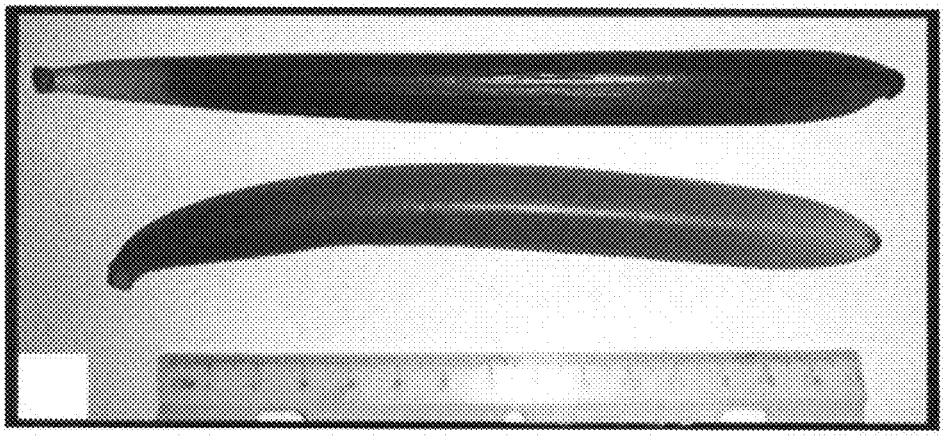
FIG. 3 illustrates green fruit (left) and fully mature, non-dehiscent fruit (right) of *vanilla* variety 'Handa'.

*Vanilla* variety 'Handa' is characterized by its aromatic fruit having a suitable vanillin content, as well as exhibiting superior agronomic and technologic properties as compared to ordinary *vanilla*, notably resistance to *Fusarium oxysporum* f. sp. *radicis vanillae* (Koyyappurath et al. 2015b), and indehiscence of the fruit. Genetic analysis using Amplified Fragment Length Polymorphism has been able to unequivocally distinguish the *vanilla* variety 'Handa' from all ordinary *vanilla* and many other *V. planifolia* varieties (Bory et al. 2008b). An image of the vines of *vanilla* variety 'Handa' bearing young fruit is presented in FIG. 1. An image of a flower of *vanilla* variety 'Handa' is presented in FIG. 2. An image of both green fruit and fully mature, non-dehiscent fruit of *vanilla* variety 'Handa' is presented in FIG. 3.

Table 2 below provides various morphological characteristics of *vanilla* variety 'Handa' as compared to those of ordinary *vanilla*.

TABLE 2

Morphological characteristics of 'Handa' as compared to ordinary vanilla

| Characteristic | 'Handa' | ordinary |
|---|---|---|
| Leaf thickness | Thick | Medium |
| Leaf: intensity of green color | Dark | Medium |
| Fruit cross section | Circular | Broad ovate |

Table 3 below provides various quantitative characteristics of the fruit of *vanilla* variety 'Handa' as compared to the fruit of ordinary *vanilla*.

TABLE 3

Quantitative Characteristics of 'Handa' fruit as compared to ordinary vanilla

| Characteristic | 'Handa' | ordinary | Relative difference(2) |
|---|---|---|---|
| Weigh of a mature fruit (g) | 25.7 (+/−3)(1) | 21.1 (+/−2.94) | +22% |
| Length of a mature fruit (cm) | 19 (+/−0.5) | 20.3 (+/−0.3) | −6% |
| Percentage of dehiscent fruits | 0 % | 98 % | Nd |
| Vanillin content of a mature fruit(3) (% dry weight) | 2.51 (+/−0.5) | 3.71 (+/−0.24) | −32% |
| ParahydroxyBenzaldehyde content(3) (% dry weight) | 0.07 (+/−0.06) | 0.08 (+/−0.03) | −13% |
| ParahydroxyBenzyl alcohol content(3) (% dry weight) | 0.2 (+/−0.08) | 0.15 (+/−0.02) | +33% |

(1)Average values measured at BRC VATEL, standard error in brackets.
(2)Calculated as follows: (Handa - Ordinary)/Ordinary
(3)Determined by HPLC analysis after enzymatic hydrolysis (Palama et al. 2011; Perez Silva et al. 2011)

The following Table 4 presents a comparison between the *vanilla* Handa and its parental cultivar ordinary *vanilla*. The Handa variety was selected by CIRAD from an offspring of self-pollination with ordinary *vanilla*. The genetic progress obtained with the Handa variety is highlighted in the following comparative Table 4:

TABLE 4

Comparison of the new variety Handa, with its parent (ordinary vanilla).

| | Ordinary vanilla (Parent) | Handa (Progeny) | Advantage of Handa vs Parent |
|---|---|---|---|
| Yield | Medium | High | Increased fruit productivity of vines |
| Fruit length | Long | Medium | |
| Fruit weight | medium | Heavy | |
| Fruit dehiscence | dehiscent | Not dehiscent | Allows the complete maturation of the pods in the field, avoids the inconveniences of scalding (loss of material, alteration of the surface of pods, handling, energy, . . . ) |
| Aropmatic profile | Bourbon-like | Bourbon-like | Aromatic profile similar to that of the ordinary vanilla (Bourbon type) |
| Susceptibility to *Fusarium* disease | Susceptible | Resistant | Better productivity and longevity of plots |

TABLE 4-continued

| Comparison of the new variety Handa, with its parent (ordinary vanilla). | | | |
|---|---|---|---|
| | Ordinary vanilla (Parent) | Handa (Progeny) | Advantage of Handa vs Parent |
| Vanillin content | hight | Medium | Fruit of Handa are about 30% less rich in vanillin, but vanillin yield per hectare is probably higher due to increased yield and longevity of vines |

The above data shows that the Handa variety of the invention is distinctly different from the parent variety (ordinary *vanilla*) in that it is more productive, resistant to *Fusarium*, and has indehiscent mature fruits. Its use can significantly increase the productivity of *vanilla* plantations.

Table 5 below provides a summary of the various advantageous characteristics of *vanilla* variety 'Handa' as compared to ordinary *vanilla*. These characteristics illustrate the advantages of using *vanilla* variety 'Handa' over ordinary *vanilla* for *vanilla* production.

TABLE 5

| Advantageous characteristics of 'Handa' as compared to ordinary vanilla | | | |
|---|---|---|---|
| Criteria | ordinary | 'Honda' | Advantage of 'Honda' over ordinary |
| Resistance to Fusarium root rot | Suscep-tible | Resistant | Increases productivity and longevity of plots. |
| Fruit weight | Medium | Heavy | Less fruits per Kg of vanilla = less manipulation per Kg. |
| Fruit dehiscence | Dehiscent | Not dehiscent | Allows fruit to reach full maturity in the filed, facilitate vanilla curing, and can compensate lower vanilla content. |

REFERENCES

Bory S., Grisoni, M., Duval, M.-F., and Besse, P. 2008a. Biodiversity and preservation of *vanilla*: present state of knowledge. Genetic Resources and Crop Evolution 55: 551-571.

Bory S., Lubinsky, P., Risterucci, A.-M., Noyer, J.-L., Grisoni, M., Duval, M.-F., and Besse, P. 2008b. Patterns of introduction and diversification of *Vanilla planifolia* (Orchidaceae) in Reunion island (Indian Ocean). American Journal of Botany 95: 805-815.

Castillo Martinez R., and Engleman, Mark E. 1993. Caracterizacion de dos tipos de *Vanilla planifolia*. Acta Botanica Mexicana 25: 49-59.

Delassus M. 1963. La lutte contre la fusariose du vanillier par les méthodes genetiques. L'agronomic tropicale 18:245-246.

Grisoni M., Anli Liachouroutu, A. K., Beson, E., Pierard, E., Liew, E. C. Y., and Alabouvette, C. Year. "Phytosanitary constraints on Bourbon *vanilla*: past and present situations and perspectives for control", In: *vanilla* 2009, D. H. Frenkel (eds)).

Hernandez Hernandez J. 2011. *Vanilla* diseases. In: D. Havkin-Frenkel & F. C. Belanger (eds). Handbook of *Vanilla* Science and Technology:26-39. Wiley-Blackwell Chichester (UK).

Koyyappurath S., Atuahiva, T., Le Guen, R., Batina, H., Le Squin, S., Gautheron, N., Edel Hermann, V., Peribe, J., Jahiel, M., Steinberg, C., Liew, E. C. Y., Alabouvette, C., Besse, P., Dron, M., Sache, I., Laval, V., and Grisoni, M. 2015. *Fusarium oxysporum* f sp. *radicis-vanillae* is the causal agent of root and stem rot of *vanilla*. Plant Pathology: n/a-n/a. 10.1111/ppa. 12445

Koyyappurath, S., Conéjero, G., Dijoux, J. B., Lapeyre Montes, F., Jade, K., Chiroleu, F., Gatineau, F., Verdeil, J. L., Besse, P., and Grisoni, M. (2015b). Differential responses of *vanilla* accessions to root rot and colonization by *Fusarium oxysporum* f. sp. *radicis-vanillae*. Frontiers in Plant Science 6. doi: 10.3389/fpls.2015.01125

Minoo D., Nirmal Babu, K., Ravindran, P. N., and Peter, K. V. 2006. Interspecific hybridization in *vanilla* and molecular characterization of hybrids and selfed progenies using RAPD and AFLP markers. Scientia Horticulturae. 108: 414-422.

Murashige T., and Skoog, F. 1962. A revised medium for rapid growth and bioassays with tobacco tissue cultures. Physiologia Plantarum 15: 473-497.

Palama T. L., Khatib, A., Choi, Y. H., Come, B., Fock, I., Verpoorte, R., and Kodja, H. 2011. Metabolic characterization of green pods from *Vanilla planifolia* accessions grown in La Réunion. Environmental and Experimental Botany 72: 258-265. DOI: 10.1016/j.envexpbot.2011.03.015

Perez Silva A., Gunata, Z., Lepoutre, J.-P., and Odoux, E. 2011. New insight on the genesis and fate of odor-active compounds in *vanilla* beans (*Vanilla planifolia* G. Jackson) during traditional curing. Food Research International 44: 2930-2937.

Roux-Cuvelier M., and Grisoni, M. 2010. Conservation and Movement of *Vanilla* Germplasm. In: E. Odoux & M. Grisoni (eds). *Vanilla:*31-41. CRC Press, Boca Raton, Fla. (USA).

Soto Arenas M. A. 1999. Filogeografia y recursos geneticos de las vainillas de México [Online]. México. Available: http://www. conabio.gob.mx/institucion/proyectos/resultados/InfJ 101.pdf [Accessed Marzo 31, 1999 2004].

Soto Arenas M. A. 2003. *Vanilla*. In: A. M. Pridgeon, P. J. Cribb, M. W. Chase & F. Ramunsen (eds). Genera orchidacearum, Vol 3, Orchidoideae (part 2):321-334. Oxford University Press.

Theis T., and Jimenez, T. A. 1957. A *vanilla* hybrid resistant to *Fusarium* root rot. Phytopathology 47: 578-581.

The invention claimed is:

1. A new and distinct variety of *vanilla* plant designated 'Handa' as shown and described herein.

* * * * *